US010827926B2

(12) United States Patent
Blackwell et al.

(10) Patent No.: US 10,827,926 B2
(45) Date of Patent: Nov. 10, 2020

(54) SYSTEMS AND METHODS FOR ASSESSING COGNITIVE FUNCTION (71) Applicant: Cambridge Cognition Limited, Cambridge (GB)

(72) Inventors: Andrew Blackwell, Cambridge (GB); Jennifer Barnett, Cambridge (GB)

(73) Assignee: Cambridge Cognition Limited, Cambridge (GB)

( * ) Notice: Subject to any disclaimer, the term of this patent is extended or adjusted under 35 U.S.C. 154(b) by 253 days.

(21) Appl. No.: 15/563,858

(22) PCT Filed: Apr. 1, 2016

(86) PCT No.: PCT/GB2016/050926
§ 371 (c)(1),
(2) Date: Oct. 2, 2017

(87) PCT Pub. No.: WO2016/156867
PCT Pub. Date: Oct. 6, 2016

(65) Prior Publication Data
US 2018/0070823 A1 Mar. 15, 2018

(30) Foreign Application Priority Data
Apr. 2, 2015 (GB) .................................. 1505707.8

(51) Int. Cl.
*A61B 5/00* (2006.01)
*A61B 5/16* (2006.01)
(Continued)

(52) U.S. Cl.
CPC .......... *A61B 5/0008* (2013.01); *A61B 5/0002* (2013.01); *A61B 5/0024* (2013.01);
(Continued)

(58) Field of Classification Search
CPC .... A61B 5/0002; A61B 5/4082; A61B 5/4088
See application file for complete search history.

(56) References Cited

U.S. PATENT DOCUMENTS 5,695,343 A 12/1997 Jabourian
6,434,419 B1 8/2002 Gevins et al.
(Continued)

FOREIGN PATENT DOCUMENTS

WO 2006/074411 A2 7/2006
WO 2012/117166 A1 9/2012

OTHER PUBLICATIONS

Nation et al., Pulse pressure is associated with Alzheimer biomarkers in cognitively normal older adults, Neurology, Dec. 3, 2013, Issue No. 81, pp. 2024-2027.
(Continued)

*Primary Examiner* — James S. McClellan
(74) *Attorney, Agent, or Firm* — Volpe Koenig (57) ABSTRACT

A method for neurological analysis and treatment is described. In one embodiment, a server sends a request to a wearable device for sensor data of a patient. The server receives sensor data from the wearable device, and sends instructions to the wearable device to present a cognitive test based on the sensor data. The server receives from the wearable device, results of the cognitive test, compares the results against a baseline, and determines an assessment of the user. A notification may be sent to the wearable device based on the assessment. A wearable device for use in the analysis and treatment is also described.

20 Claims, 3 Drawing Sheets (51) Int. Cl.
*A61B 5/11* (2006.01)
*G16H 40/63* (2018.01)
*A61B 5/02* (2006.01)
*G06F 19/00* (2018.01)
*A61B 5/053* (2006.01)

(52) U.S. Cl.
CPC .............. *A61B 5/02* (2013.01); *A61B 5/1118* (2013.01); *A61B 5/16* (2013.01); *A61B 5/165* (2013.01); *A61B 5/168* (2013.01); *A61B 5/6801* (2013.01); *G06F 19/3418* (2013.01); *G06F 19/36* (2013.01); *G16H 40/63* (2018.01); *A61B 5/0531* (2013.01)

(56) References Cited

U.S. PATENT DOCUMENTS

| | | | |
|---|---|---|---|
| 8,950,864 | B1 | 2/2015 | Massengill |
| 2005/0159671 | A1 | 7/2005 | Sneddon |
| 2007/0149952 | A1* | 6/2007 | Bland ............... G16H 50/20 604/890.1 |
| 2010/0041621 | A1* | 2/2010 | Renshaw ............ A23L 33/10 514/51 |
| 2011/0060252 | A1* | 3/2011 | Simonsen ........... A61B 5/0488 600/595 |
| 2012/0130266 | A1 | 5/2012 | Mathan et al. |
| 2013/0224117 | A1 | 8/2013 | Royall et al. |
| 2013/0237772 | A1* | 9/2013 | Pisani .................. A61B 5/0002 600/301 |
| 2014/0154651 | A1 | 6/2014 | Stack |
| 2014/0187648 | A1 | 7/2014 | Howard et al. |
| 2015/0202447 | A1* | 7/2015 | Afshar ............... A61B 5/04012 600/378 |

OTHER PUBLICATIONS

Poh, et al., Autonomic changes with seizures correlate with postictal EEG suppression, Neurology, Jun. 5, 2012, Issue No. 78, pp. 1-10.
Yamakawa et al., Caring for early-onset dementia with excessive wandering of over 30 kilometres per day: a case report, Psychogeriatrics, 2014, Issue No. 14, pp. 255-260.
O'Mahony et al., Objective diagnosis of ADHD using IMUs, Medical Engineering & Psysics, 2014, Issue No. 36, pp. 922-926.
McIntosh et al., When the social mirror breaks: deficits in automatic, but not voluntary, mimicry of emotional facial expressions in autism, Developmental Science, 2006, Issue No. 9:3, pp. 295-302.
Thomée et al., Mobile phone use and stress, sleep disturbances, and symptoms of depression among young adults—a prospective cohort study, BMC Public Health, 2011, Issue No. 11:66, pp. 1-11.
Ikeda et al., Association between mobile phone use and depressed mood in Japanese adolescents: a cross-sectional study, Environ Health Prev Med, 2014, Issue No. 19, pp. 187-193.
Choudhury et al., Predicting Depression via Social Media, Proceedings of the Seventh International AAAI Conference on Weblogs and Social Media, 2013, pp. 128-137.
Chamberlain et al., Translational Approaches to Frontostriatal Dysfunction in Attention-Deficit/Hyperactivity Disorder Using a Computerized Neuropsychological Battery, Biol Psychiatry, 2010, pp. 1-12.
Tanaka et al., Voice features of Parkinson's disease patients with subthalamic nucleus deep brain stimulation, J Neurol, 2015, pp. 1173-1181.
Blackwell et al, Detecting Dementia: Novel Neuropsychological Markers of Preclinical Alzheimer's Disease, Dementia and Geriatric Cognitive Disorders, 2004, Issue No. 17, pp. 42-48.
Owen et al, Fronto-striatal Cognitive Deficits at Different Stages of Parkinson's Disease, Brain, 1992, Issue No. 115, pp. 1727-1751.
Rock et al., Cognitive impairment in depression: a systematic review and meta-analysis, Psychological Medicine, 2014, Issue No. 44, pp. 2029-2040.
Clark et al, Sustained Attention-Deficit Confirmed in Euthymic Bipolar Disorder but Not in First-Degree Relatives of Bipolar Patients or Euthymic Unipolar Depression, Biol Psychiatry, 2015, Issue No. 57, pp. 183-187.
Gmeindl et al., Deconstructing Spatial Working Memory and Attention Deficits in Multiple Sclerosis, Neuropsychology, Jan. 2012, Issue No. 26, pp. 57-70.
Marinus et al., Assessment of Sleep and Sleepiness in Parkinson Disease, Sleep, 2003, vol. 26, No. 8, pp. 1049-1054.
Terán-Santos et al., The Association Between Sleep Apnea and the Risk of Traffic Accidents, The New England Journal of Medicine, Mar. 18, 1999, vol. 340, Issue No. 11, pp. 847-851.
Abe et al., Early Detection System Considering Types of Dementia by Behavior Sensing, IEEE 2nd Global Conference, on Consumer Electronics (GCCE), 2013, pp. 348-349.
Galambos et al., Management of Dementia and Depression Utilizing In-Home Passive Sensor Data, Gerontechnology, Jan. 1, 2013, vol. 11, Issue No. 3, pp. 457-468.
Hoffmeyer et al., Sensor Based Monitoring for People with Dementia: Searching for Movement Markers in Alzheimer's Disease for a Early Diagnostic, Hamiltonian Mechanics for People with Dementia, 2012, pp. 137-145.
Kaegi-Trachsel et al., Mental Health Decline Prediction: A Smart Sensor for Day to Day Activity Recognition, HEALTHINF, Proceedings of the International Conference on Health Informatics, Jan. 26-29, 2011, pp. 219-227.
Martinez et al, Supporting Diagnostic Decision for Early Detection of a Neurodegenerative Disease on a Behavioural Altered Pattern Basis, IADIS International Conference e-Health 2011, pp. 81-88.

* cited by examiner

SYSTEMS AND METHODS FOR ASSESSING COGNITIVE FUNCTION

FIELD OF THE INVENTION

This invention relates to systems and methods for assessing cognitive function and symptoms of neurological and neuropsychiatric conditions. It is particularly, but not exclusively, concerned with methods which use results from wearable sensor(s) to initiate cognitive testing.

BACKGROUND OF THE INVENTION

Brain health has a huge impact on wellbeing throughout life. Cognitive functions such as memory, concentration, and mental agility drive educational attainment, work productivity and leisure activities. Sub-optimal cognition is personally and societally expensive, whether caused by environmental influences such as diet and stress, or long term conditions such as depression or dementia. The UK government's 2008 Foresight report on Mental Capital and Wellbeing identified finding ways to maintain cognitive capital as a major challenge that needs tackling so the aging population can remain independent and economically productive for longer.

With an aging population in many countries, neurological disorders associated with old-age, such as dementia, are also increasingly prevalent.

For example, dementia is a common and costly condition. Researchers estimate that dementia affects between 2.4 to 5.5 million Americans. By 2050, the prevalence of Alzheimer's disease is projected to be 13.8 million people in the United States, with approximately 1 million new cases a year. The estimated total health, long-term, and hospice care costs for dementia in the United States were $200 billion in 2012. Medicare and Medicaid pay approximately 70 percent of these costs, representing $140 billion. These costs do not include the estimated $210 billion in uncompensated care that informal caregivers provide annually.

The prevalence of dementia is strongly related to increasing age. Data from large population-based surveys indicate that the prevalence of dementia in the United States is 5 percent in individuals at ages 71 to 79 years, rising to 24 percent at ages 80 to 89 years, and 37 percent in those older than age 90 years. These prevalence estimates, however, are highly dependent on the methods and operational criteria used for diagnosis. An international Delphi consensus and review of published dementia prevalence studies estimated mean prevalence in the United States and Canada at 0.8 percent (standard deviation [SD], 0.1) in individuals ages 60 to 64 years, 1.7 percent (SD, 0.1) in individuals ages 65 to 69 years, 3.3 percent (SD, 0.3) in individuals ages 70 to 74 years, 6.5 percent (SD 0.5) in individuals ages 75 to 79 years. 12.8 percent (SD. 0.5) in individuals ages 80 to 84 years, and 30.1 percent (SD, 1.1) in individuals age 85 years or older.

Cognitive health is harder to measure than physical parameters such as blood pressure or cholesterol but scientifically-validated cognitive testing has become an established tool in assessing brain health.

Cognitive assessment tests were originally developed as pen-and-paper tests, and continue to be available in that format from large educational and clinical psychology suppliers such as Pearson Assessment. Computerised cognitive assessment is a rapidly growing area but the existing assessments are generally marketed to healthcare professionals, academics and pharmaceutical companies and are not in a suitable format for direct access by individuals or patients.

Measures such as memory function, reaction times and other physical parameters can be assessed by cognitive function testing and can be an important aid for clinicians in detecting risk for and making a diagnosis of neurological and neuropsychiatric conditions and thereafter monitoring the status of the condition and the influence of any therapeutic regime prescribed to the patient.

Cognitive testing can play an important role in several ways in the management of neurological disorders or general brain health:

(1) providing baseline information for a subject to assess risk for a condition or as part of a study providing normative data for a particular population;
(2) providing a means to detect early signals of the onset of neurological disorders or their precursors;
(3) to aid in the accurate diagnosis of neurological disorders;
(4) to monitor the course of neurological disorders; and
(5) to determine the impact that a course of treatment is having on the patient in terms of both cognitive safety and efficacy.

Cognitive function testing can aid in the diagnosis of dementia and other neurological conditions or neuropsychiatric conditions.

Cognitive function testing typically takes the form of a series of discrete tests undertaken by the subject under the supervision of a clinician. The tests are scored against previous test data for the patient or against historic data sets for relevant populations with normal cognitive function and those with known neurological disorders. The relevant population may be selected by reference to age, gender and known medical conditions.

Examples of current cognitive function tests for dementia and other neurological disorders are the Mini Mental State Examination, the Abbreviated Mental Test, the General Practitioner Assessment of Cognition, and the Hopkins Verbal Learning Test.

There are a number of known disadvantages to current methodologies of cognitive function testing which can lead to the introduction of errors or bias into results. Typically, the testing is carried out overtly through a formal question/answer format. For example, the subject is usually assessed:

(1) at a small number of discrete time points—often only once;
(2) in a medical environment under the supervision of a medical professional such as a doctor or nurse;
(3) by conscious response which may be affected by the test environment.

The potential limitations with such systems are well-known:

Assessments which rely on verbal cues and responses are problematic in the hard of hearing Some assessments require motor skills or tools such as paper, pencil and calculators (http://qjmed.oxfordjournals.org/content/100/8/469)

The ecological validity (extent to which the cognitive testing reflects real-world cognitive function) is often questionable:
(http://www.ncbi.nlm.nih.gov/pubmed/15000225;
http://www.ncbi.nlm.nih.gov/pubmed/20609481;
http://www.sciencedirect.com/science/article/pii/S0887617706000527)

The testing environment can negatively impact the individual's cognitive scores in a manner analogous to 'white-coat hypertension'

Whilst techniques are available to reduce such errors, these factors may limit the utility of the test results for the clinician who is seeking to make a diagnosis or for a pharmaceutical company developing new drugs.

Better methods of assessing cognitive function and neurological conditions are therefore required.

There is also a developing interest in providing access to cognitive function testing to the population outside of the clinical setting and providing means for self-assessment or monitoring of cognitive function.

Indeed, there is a growing consumer interest in optimising cognition throughout life, as evidenced by the 'brain training' market. Optimising cognition requires changes in lifelong behaviours such as diet, exercise and substance use, because brain health is driven by the same factors as cardiovascular health. Shorter-term fluctuations in cognition are driven by moment-to-moment and daily cycles of factors such as wakefulness and tiredness, intake of caffeine, nicotine, carbohydrates, etc, and stress-related changes in neurochemicals such as adrenaline and cortisol. Consumers need a way of tracking and visualising this so they can understand the effects of their short- and long-term behaviours on their brain health.

Self-testing is widely used to measure indicators of physical health and fitness but is not yet available in a convenient and reliable format for indicators of mental health or well-being.

For example, wearable technology is widely used to monitor the physical fitness of a user, particularly during exercise such as walking, running, cycling or swimming. Numerous parameters may be measured during exercise such as the distance covered, time taken, the total ascent gained during the exercise, the route taken, heart rate and speed. The wearable technology may be, for example, in the form of a device, watch or smartphone or glasses.

Exercise data is typically recorded by the device and is capable of visualisation and analysis on a computer screen, which may be part of the wearable device or a separate computer system with which the device can communicate. The data from the physical exercise is recorded and can be analysed in many ways, such as by comparison against previous results to indicate trends in physical performance.

There is also a large, as yet unmet, medical need for the better understanding and self-management of brain health. The WHO estimates that brain disorders cause one-third of the burden of all diseases and much of the risk is modifiable: half of a person's risk for Alzheimer's disease is driven by seven lifestyle-related factors such as diet, exercise, and smoking. The possibility to use lifestyle to manage brain health is therefore of benefit to the individual and society.

Empowering individuals to manage their own health is likely to reduce healthcare costs. It is estimated that the NHS in England could save £4.4 billion a year if it adopted innovations that involves patients, families and communities more directly in the management of long term health conditions.

Since the lifestyle factors that drive better brain health largely overlap with those that prevent cancer, heart disease and other physical conditions or illnesses, motivating improvements in brain health would be expected to have large and positive consequences on all the major chronic diseases of mid- and late-life.

As well as direct medical costs, self-management of brain health can bring additional economic opportunity. Much of the cost associated with brain disorders comes from loss of employment of patients and carers, and supporting the development of new tools to better manage and treat these highly prevalent conditions is an important part of supporting employment and economic productivity among patients and their caregivers. For example the total cost of dementia in the EU in 2008 was estimated at €160 billion, of which 56% were costs associated with informal care. More broadly, cognitive problems such as poor concentration, memory lapses, and risky decision-making have widespread impacts on an individual's overall productivity, through un- and under-employment, reduced educational achievement, and lower efficiency and creativity at work.

Furthermore, educating and informing patients and other consumers about brain health can help reduce the stigma surrounding mental health and conditions such as dementia and empower patients to make better decisions about when and how to seek help.

Improving tools for the self-management of brain health may ultimately improve equality of access to healthcare. Many patients with brain conditions cannot access effective treatment, for example access only 21% of UK patients have access to modern multiple sclerosis drugs. Across Europe, two thirds of people with brain disorders receive no treatment and many others have additional uncontrolled symptoms which worsen the impact of the disorders. For example, up to 70% of people with epilepsy could lead normal lives if properly treated, but for a majority this is not the case.

Such direct to consumer cognitive testing is at present minimal because available products are not well-suited for consumer use. The nearest comparable field at present is so-called "brain training" which has been reasonably well served by both web-based and smartphone applications but is limited by a lack of scientific validity and therefore utility, particularly in the clinical sphere.

Attempts to improve cognitive function through 'brain-training' have become popular due to the fun and immersive nature of computer- and web-based brain training programmes. Brain training describes the process of using repeated practise on games or puzzles to improve performance in one or more areas of cognitive performance. These programmes claim to work by changing the plasticity of the brain. However large-scale assessments of such programmes suggest that while performance on the specific task that is practised improves, they are not effective in producing any more generalised improvements in cognitive performance. In order to demonstrate to the consumer the efficacy of the programme, brain training tools sometimes include game-like measurement of cognitive domains before and after a period of training. However the core of brain training is a focus on the intervention rather than cognitive assessment per se and an intention to improve cognitive function. These programmes are not designed to measure disease risk, change in disease state, or motivate or monitor changes in lifestyle, behaviour, or other factors outside of the brain training system.

For pharmaceutical companies developing new drugs to treat neurological conditions, the ability to monitor cognitive function on an ongoing basis offers the potential to transform the way in which data from clinical studies is generated and analysed in order to assess the safety and/or efficacy of the new drugs.

The provision of mobile or ongoing cognitive assessments may prove valuable in demonstrating the efficacy of new treatments for disorders such as Alzheimer's, as well as the safety of medicines which could potentially impair concentration or decision-making. Current "gold standard"

assessments take place in clinical settings and therefore can only provide a snapshot of cognitive performance.

Technological developments which can assist in the development and testing of treatments for neurological conditions are urgently needed because approval rates for new brain-related drugs are low, causing pharmaceutical companies to seek better ways to run clinical trials and more accurate ways to target individuals who may be at a high risk of disorders such as Alzheimer's.

An object of aspects of the present invention is to provide methods and systems which assist in providing improved cognitive monitoring to assist in monitoring the effects of medical treatment on cognition in respect of safety and/or efficacy. The term "medical treatment" used herein includes the use of an approved or licensed medicinal product with a marketing authorisation or the use of an investigational medicinal product.

Fun 'brain tests' are already readily available to consumers but these lack scientific validity and so are of no real use in measuring performance, assessing risk for brain disorders, or monitoring the effects of interventions. Such "brain games" are not used to inform medical decisions and have no validity in assessing cognitive function and how it is influenced by lifestyle choices.

The use of sensors and computer systems to monitor physical parameters and to provide feedback to the user and or health professionals is well-known in the art. For example, such systems are commonly used to record physical performance of athletes by tracking speed, distance, location and heart rate.

Computer systems utilising sensors to monitor a patient's physical parameters are also known in the art and can be used to monitor safety conditions of workers, members of the armed forces and patients in healthcare settings for certain conditions. Such sensors are concerned with the measurement of physical parameters and do not provide any monitoring of cognitive function.

SUMMARY OF THE INVENTION

At their broadest, aspects of the present invention provide systems and methods for monitoring individuals which measure a physical parameter associated with the individual and, based on comparison of that measured parameter with one or more baselines, initiate cognitive tests for the individual to perform.

A first aspect of the present invention preferably provides a system for monitoring an individual, the system including: a wearable sensor for measuring at least one physical parameter associated with the individual; a memory storing a predetermined baseline of either normal behaviour for that parameter or of abnormal behaviour for that parameter and a predetermined baseline for a cognitive test; a processor that: compares the parameters measured by the sensor to said baseline, and if either: the measured physical parameter deviates from the baseline of normal behaviour by more than a pre-defined amount, or the measured physical parameter matches the baseline of abnormal behaviour within a pre-determined tolerance, triggers at least one cognitive test for the individual to perform; and compares the results of said cognitive test to a further predetermined baseline, and a user interface for presenting cognitive tests to the individual and recording the individual's responses.

Accordingly, a system according to the present aspect can use cognitive testing in conjunction with physical behavioural data in the monitoring of brain health through wearable technology.

Behavioural data can be collected from passive monitoring of the sensor and/or from active monitoring based on the individual's responses to cognitive tests carried out through the user interface.

The system can monitor the collective behavioural data in real time and compares the data against baselines which include one or more of: historic data of the user; relevant validated data sets for general populations; and relevant validated data sets for populations with specific neurological disorders.

The system is particularly useful for assessing cognitive function, detecting and monitoring symptoms of neurological and neuropsychiatric conditions and other fluctuations in brain health caused by lifestyle choices, such as diet, sleep, exercise, consumption of alcohol or caffeine.

The system can use physical data from the wearable sensor together with validated cognitive tests to obtain behavioural data of the individual and provide real time analysis from the user in a manner that is not achievable through traditional clinically-based cognitive tests. Such data may be valuable in diagnosing and/or monitoring neurological and neuropsychiatric conditions and also in monitoring and reporting the fluctuations in brain health due to lifestyle influences. Given the established links between lifestyle influences and certain disorders, the potential for individuals to monitor their brain health and thus provide an opportunity to modify their behaviour and thus manage known risk factors for serious disorders is of great utility.

The processor may be arranged to notify the individual or a third party of the measured physical parameter; the results of the cognitive test and/or the comparison of said results against the further baseline. This can allow the individual to keep themselves personally informed of developments in their cognitive function. A third party, such as a doctor, carer or relative may also be informed, particularly if the measurements/results indicate an increased risk to the individual which may allow preventative measures to be taken or assistance rendered.

In some embodiments of the present aspect, the system further includes a remote server having the memory and the processor, and wherein the wearable sensor and the user interface are communicatively linked to said server. The remote server can store significant quantities of baseline information for the comparisons, and these stored baselines can be used across a wide range of individuals using systems according to the present aspect. The use of a remote server reduces the amount of storage and processing power required local to the individual.

In alternative embodiments, the system further includes a computer local to the individual, the computer having the memory and the processor, and wherein the wearable sensor and the user interface are communicatively linked to the computer. The local computer may be a smartphone, smartwatch, tablet, laptop or desktop computer, or may form part of a television set. In these embodiments the local computer is able to carry out the comparisons, leading to fast responses without any reliance on an active communications link.

In such embodiments, the computer may further include the user interface or the wearable sensor, or both.

It will be appreciated that embodiments of the system could include both one or more remote servers and a local computer, with the functions of the processor and the memory being divided between processors and memories in the remote servers and the local computer. For example, the remote server may store baseline data relating to the general population, whilst the local computer may store data relating to the individual and comparisons may be made against both of these.

The system of the present aspect can also allow the analysis of behavioural data (physical and cognitive) in real time and the instruction via a wearable device for the individual to conduct additional cognitive testing. Such additional assessments can be selected by the system as appropriate to the behavioural data previously obtained. The response of the individual to such additional validated cognitive assessments can provide important additional data useful in the management of neurological or neuropsychiatric disorders and may be useful in the elimination of false positive results.

The system of the present aspect can enable frequent in-field assessment of the individual's physical and neurological condition. The results from the system can be cross-validated to established healthcare standards. The system may also be programmable and reactive to allow real-time export of data and updating of the various components of the system according to pre-programmed protocols; and it can summarise datapoints in a time-sensitive and personally meaningful way—allowing benchmarking against factors such as drug dosage or sleep patterns.

In addition, the system may monitor fluctuations in brain health of any individual enabling the individual to monitor the influence that their lifestyle choices, such as diet, sleep, exercise, consumption of alcohol or caffeine, have on their cognitive function.

The computer system can display feedback to the individual and/or to the individual's carer or health professional regarding the current cognitive function of the individual and suggested actions. The feedback can be made appropriate to the relevant recipient, whether the individual, carer or health professional.

Where the system identifies a risk to health or that the cognitive performance of the individual is outside normal values, the system can display relevant messages or information to the individual on the user interface and/or activate additional cognitive tests or questions through the user interface, preferably through a wearable device and/or a smartphone. The individual's response to such tests, taken together with all previous behavioural data, can be further analysed and compared against historic data of the user and relevant validated data sets for both the general populations and populations with neurological disorders. The system may then provide additional feedback to the individual and/or the carer and/or the health professional responsible for the user. Additionally, the individual's carers or health professionals may be able to access the system remotely to display such messages or information or activate additional cognitive tests or questions, or obtain further information, such as historic data from the sensor.

The system may also collect physical exercise data which can be augmented by cognitive testing to show the influence of exercise on cognition whether in the general population or in patients with neurological disorders.

The system may operate using the method of the second aspect described below, including some, all or none of the optional and preferred features of that aspect. However, the system may also operate using alternative methods.

The system may include some, all or none of the preferred and optional features described above in relation to the system, or more generally below.

A second aspect of the present invention provides a method of monitoring an individual, the method including the steps of: repeatedly measuring at least one physical parameter associated with the individual using a sensor worn by the individual; comparing the measurements of said physical parameter against a predetermined baseline of either normal behaviour for that parameter or of abnormal behaviour for that parameter; if either: the measured physical parameter deviates from the baseline of normal behaviour by more than a pre-defined amount, or the measured physical parameter matches the baseline of abnormal behaviour within a predetermined tolerance, triggering at least one cognitive test for the individual to perform and recording the results; and comparing said results against a further predetermined baseline.

Accordingly, a method according to the present aspect can use cognitive testing in conjunction with physical behavioural data in the monitoring of brain health through wearable technology.

Behavioural data can be collected from passive monitoring of the sensor and/or from active monitoring based on the individual's responses to cognitive tests carried out through the user interface.

The method can monitor the collective behavioural data in real time and compares the data against baselines which include one or more of: historic data of the user; relevant validated data sets for general populations; and relevant validated data sets for populations with specific neurological disorders.

The method is particularly useful for assessing cognitive function, detecting and monitoring symptoms of neurological and neuropsychiatric conditions and other fluctuations in brain health caused by lifestyle choices, such as diet, sleep, exercise, consumption of alcohol or caffeine.

Thus the second aspect can provide a method of monitoring and/or diagnosing and/or managing individuals with neurological or neuropsychiatric disorders.

The method can use physical data from the wearable sensor together with validated cognitive tests to obtain behavioural data of the individual and provide real time analysis from the user in a manner that is not achievable through traditional clinically-based cognitive tests. Such data may be valuable in diagnosing and/or monitoring neurological and neuropsychiatric conditions and also in monitoring and reporting the fluctuations in brain health due to lifestyle influences. Given the established links between lifestyle influences and certain disorders, the potential for individuals to monitor their brain health and thus provide an opportunity to modify their behaviour and thus manage known risk factors for serious disorders is of great utility.

The method may include the further step of notifying the individual or a third party of the measured physical parameter; the results of the cognitive test and/or the comparison of said results against the further baseline. This can allow the individual to keep themselves personally informed of developments in their cognitive function. A third party, such as a doctor, carer or relative may also be informed, particularly if the measurements/results indicate an increased risk to the individual which may allow preventative measures to be taken or assistance rendered.

The method of the present aspect can also allow the analysis of behavioural data (physical and cognitive) in real time and the instruction via a wearable device for the individual to conduct additional cognitive testing. This additional testing may be initiated on a periodic basis. Such additional assessments can be selected by the computer system as appropriate to the behavioural data previously obtained. The response of the individual to such additional validated cognitive assessments can provide important additional data useful in the management of neurological or neuropsychiatric disorders and may be useful in the elimination of false positive results.

In a development of the method the physical parameter measured may be recorded over time and used to update one or more baselines for that parameter. Thus a history of that physical parameter can be stored for the individual and used as a basis for future comparisons.

The method of the present aspect can enable frequent in-field assessment of the individual's physical and neurological condition. The results can be cross-validated to established healthcare standards. The method may also be reactive to allow real-time export of data and updating according to pre-determined protocols; and it can summarise datapoints in a time-sensitive and personally meaningful way—allowing benchmarking against factors such as drug dosage or sleep patterns.

In addition, the method may monitor fluctuations in brain health of any individual enabling the individual to monitor the influence that their lifestyle choices, such as diet, sleep, exercise, consumption of alcohol or caffeine, have on their cognitive function.

The method can provide feedback to the individual and/or to the user's carer or health professional regarding the current cognitive function of the user and suggested actions. The feedback can be made appropriate to the relevant recipient, whether the individual, carer or health professional.

Where the method identifies a risk to health or that the cognitive performance of the individual is outside normal values, relevant messages or information can be displayed to the individual and/or additional cognitive tests or questions initiated, preferably through a wearable device and/or a smartphone. The individual's response to such tests, taken together with all previous behavioural data, can be further analysed and compared against historic data of the user and relevant validated data sets for both the general populations and populations with neurological disorders. Additional feedback may then be provided to the individual and/or the carer and/or the health professional responsible for the user. Additionally, the individual's carers or health professionals may be able to cause such messages or information to be displayed to the user or activate additional cognitive tests or questions, or obtain further information, such as historic data from the sensor.

The method may also collect physical exercise data which can be augmented by cognitive testing to show the influence of exercise on cognition whether in the general population or in patients with neurological disorders.

The method may use the system of the above described first aspect, including some, all or none of the optional and preferred features of that aspect. However, the method may also use alternative systems.

The method may include some, all or none of the preferred and optional features described above in relation to the method, or more generally below.

At their broadest, further aspects of the present invention provide systems and methods for monitoring the cognitive function of individuals undergoing medical treatment.

A third aspect of the present invention provides a system for monitoring the cognitive function of an individual undergoing medical treatment, the system comprising:

a processor; and
a user interface,
wherein the processor periodically initiates a cognitive test on the user interface to be performed by the individual, compares the results of the test against a stored predetermined baseline in order to assess the individual's cognitive function.

The term "medical treatment" used here includes the use of an approved or licensed medicinal product with a marketing authorisation or the use of an investigational medicinal product.

Preferably the user interface and processor form part of a portable or wearable system operated by the individual.

The system may further include a remote server, wherein the processor is located in the remote server and the user interface is local to the individual and in communication with the remote server. The relative advantages of providing the processor locally or in a remote server have been discussed in relation to the first aspect above. In many embodiments, the functions of the processor will be split between a processor in a local device, such as a portable or wearable system operated by the individual and a remote server.

The system may further include a wearable sensor that is configured to measure at least one physical parameter of the individual, the processor comparing the measured parameter against a predetermined baseline, and including the results of said comparison in the assessment of the individual's cognitive function.

In certain embodiments, the user interface and wearable sensor are part of a single device worn by the user.

For pharmaceutical companies developing new drugs to treat neurological conditions, the ability to monitor cognitive function on an ongoing basis using a system according to this aspect can potentially transform the way in which data from clinical studies is generated and analysed in order to assess the safety and/or efficacy of the new drugs.

For example, the provision of mobile and/or ongoing cognitive assessments may prove valuable in demonstrating the efficacy of new treatments for disorders such as Alzheimer's, as well as the safety of medicines which could potentially impair concentration or decision-making. The ongoing nature of the tests and information gathered in a non-clinical environment can provide a wealth of information for the assessment of either the efficacy of a treatment or the side-effects of a treatment.

Analogous to the use of mobile blood pressure monitors, mobile or ongoing cognitive monitoring may allow researchers to measure and monitor a treatment's effects on day-to-day fluctuations in cognition, and interactions with food and drink, sleep, physical activity, and other medicines. It may improve clinical trials by providing a more accurate baseline from which to measure a treatment's effects and a new means to remotely monitor the safety of new drugs.

By gathering information about cognitive performance in the patient's own environment rather than in laboratory contexts, and allowing data collection more frequently, there will be a better chance to detect real drug effects among the environmental 'noise' and without the drawbacks of clinical and lab settings (e.g. white coat syndrome). This improved signal:noise ratio may allow companies to detect significant drug effects in smaller samples (accelerating the drug development process) and make logistically practical longer, more representative and less localised clinical trials to occur, by substituting remote monitoring for more expensive face-to-face interactions. This latter use may be particularly important in allowing companies to monitor large numbers of patients for potential cognitive safety concerns over long periods of time, potentially encouraging regulators to make new treatments available sooner where there is high unmet medical need.

The system of this aspect may also be useful in reducing the incidences of false positive data by assessing the totality of behavioural data and using follow-up cognitive testing based on changes to physical parameters.

Preferably the medical treatment is intended to treat a neurological disorder. The system of this aspect can thus be used in the clinical development of agents for the treatment of neurological disorders, such as those listed below.

The system of this aspect may operate using the method of the fourth aspect described below, including some, all or none of the optional and preferred features of that aspect. However, the system may also operate using alternative methods.

The system may include some, all or none of the preferred and optional features described above in relation to the system, or more generally below.

A fourth aspect of the present invention provides a method of monitoring the cognitive function of an individual for assessing the effects of a medical treatment being taken by the individual, the method including the steps of: periodically initiating a cognitive test to be performed by the individual; communicating the results of said test to a computer; comparing the results of the test against a predetermined baseline to assess the individual's cognitive function.

The method of this aspect may further include the steps of: measuring at least one physical parameter of the individual using a sensor worn by the individual; comparing the measurements of said physical parameter against a predetermined baseline; and using said comparison in the assessment of the individual's mental state.

For pharmaceutical companies developing new drugs to treat neurological conditions, the ability to monitor cognitive function on an ongoing basis using a method according to this aspect can potentially transform the way in which data from clinical studies is generated and analysed in order to assess the safety and/or efficacy of the new drugs.

For example, the provision of mobile and/or ongoing cognitive assessments may prove valuable in demonstrating the efficacy of new treatments for disorders such as Alzheimer's, as well as the safety of medicines which could potentially impair concentration or decision-making. The ongoing nature of the tests and information gathered in a non-clinical environment can provide a wealth of information for the assessment of either the efficacy of a treatment or the side-effects of a treatment.

For an individual patient, and their carer and healthcare professionals, the ability to monitor cognitive function on an ongoing basis using a method according to this aspect can provide useful information to help determine if a particular course of treatment is of benefit to that specific patient.

Analogous to the use of mobile blood pressure monitors, mobile or ongoing cognitive monitoring may allow researchers to measure and monitor a treatment's effects on day-to-day fluctuations in cognition, and interactions with food and drink, sleep, physical activity, and other medicines. It may improve clinical trials by providing a more accurate baseline from which to measure a treatment's effects and a new means to remotely monitor the safety of new drugs.

By gathering information about cognitive performance in the patient's own environment rather than in laboratory contexts, and allowing data collection more frequently, there will be a better chance to detect real drug effects among the environmental 'noise' and without the drawbacks of clinical and lab settings (e.g. white coat syndrome). This improved signal:noise ratio may allow companies to detect significant drug effects in smaller samples (accelerating the drug development process) and make logistically practical longer, more representative and less localised clinical trials to occur, by substituting remote monitoring for more expensive face-to-face interactions. This latter use may be particularly important in allowing companies to monitor large numbers of patients for potential cognitive safety concerns over long periods of time, potentially encouraging regulators to make new treatments available sooner where there is high unmet medical need.

The method of this aspect may also be useful in reducing the incidences of false positive data by assessing the totality of behavioural data and using follow-up cognitive testing based on changes to physical parameters.

Preferably the medical treatment is intended to treat a neurological disorder. The method of this aspect can thus be used in the clinical development of agents for the treatment of neurological disorders, such as those listed below.

Preferably the cognitive function of the individual is monitored to determine the effectiveness of the medical treatment in treating a neurological disorder.

The method may use the system of the above described first aspect, including some, all or none of the optional and preferred features of that aspect. However, the method may also use alternative systems.

The method may include some, all or none of the preferred and optional features described above in relation to the method, or more generally below.

The following possibilities, alternatives, preferred and optional features are applicable to all of the above described aspects.

The wearable sensor(s) are preferably incorporated in one or more wearable devices. Wearable devices incorporating sensors are well known. As used herein the term wearable device means any device that is portable and that a user can carry with them and includes a means of communicating with the other parts of the system, preferably through wireless technology. The wearable device may itself include a user interface which is able to present information to the individual and receiving inputs, such as responses or commands from the individual.

The wearable device may be a watch, band, glasses or a smartphone. The wearable device may be an item of clothing, such as a belt or shoes, or an item of jewelry such as a broach, pendant, ring or earring or may be embedded into such items. The wearable device may be implanted on the body of the user—for example in dentures, prosthetic or subcutaneously. Particular examples of wearable devices include an Apple Watch, an Android Wear watch, Google Glass or a smartphone such as an iPhone or an Android smartphone.

The user may be presented with visual or audible information by the wearable device. Visual information may be displayed on a screen or projected onto a surface. Audible information may be delivered via a speaker or via headphones or an earpiece. The wearable sensor/device preferably communicates with the other parts of the system through wireless technology. Several wireless technology standards are known in the telecommunications industry and include 3G, 4G, Bluetooth and Wi-Fi.

The term sensor as used herein refers to any device that can measure one or more physical parameters of the user. Examples of some physical parameters that are relevant in the assessment of particular neurological disorders or cognitive function are set out below:

Pulse/ECG
Skin Conductance
Location

Activity and/or Acceleration in multiple dimensions (ie movement)

Voice parameters such as pitch, frequency, speed of talking, use of key words.

Use of wearable device/smartphone itself—use of phone and message functions, use of other applications or programmes installed on the phone, number of times phone is checked, response speed to incoming stimuli eg a phone call Blood pressure Visual recognition of facial expression Electromagnetic field to measure brain activity body temperature fluctuations polysomnography For example, the sensor may be a heart rate monitor, a blood pressure monitor, a GPS tracker, an accelerometer, a location tracker, a microphone, or a camera.

The system may comprise one or a multiplicity of such sensors and may have sensors measuring different parameters or a plurality of sensors measuring the same parameter.

The sensor may be embedded in a wearable device. A sensor may be the wearable device. For example, the wearable device may display cognitive tests and measure the response or reaction times of the user as one behavioural parameter that is sensed and monitored by the computer system.

The processor may be located in the wearable device or it may be in a separate computing device such as a smartphone, tablet computer, laptop computer or desktop computer. The processor collects and processes the behavioural data (and may store it in a memory device such as a RAM memory, flash memory or a hard disk) and is able to process the said data through the use of appropriate computer software or, optionally, is able to transmit the said data to a remote server for analysis and receive information and commands from the remote server. The processor carrying out the comparisons may alternatively be located in the remote server.

Cognitive testing software is known in the art for many neurological disorders (such as Cantab Mobile and Cogstate's Cognigram for dementia and mild cognitive impairment, BrainCare by NeuroTrax for monitoring recovery after stroke or traumatic brain injury).

The Applicant is a developer and supplier of validated cognitive testing software to academic scientists, the pharmaceutical industry and general practitioners. The software comprises different selections from a base library of >20 individual computerised cognitive tests and present these tests in orders and administration modes suitable to the testing environment and user. The tests have been validated over a period of up to 25 years through academic and clinical studies in healthy volunteer and patient populations.

Behavioural data includes the data from the sensor and wearable device whether as a result of passive monitoring, active monitoring or a combination of both passive and active monitoring.

For example, behavioural data can include physical parameters and behaviour of the user such as pulse, patterns of physical activity (or lack thereof), speech patterns, response times in cognitive tests delivered via the wearable device.

Behavioural data may include user identified inputs regarding lifestyle such as dietary information.

The behavioural data is preferably monitored in real time. his means that the computer system is capable of monitoring the output from the sensor and wearable device as and when the data is generated by the user and processing the data in a short time period thereafter, such that the results of the processing are available on a timescale which means that the results accurately reflect the current status of the individual.

As used herein, neurological disorder means any disorder of the brain and nervous system together with neuropsychiatric disorders.

The US National Institute of Health's National Institute of Neurological Disorders and Strokes (NINDS) maintain an A-Z of neurological disorders on its website (http://www.ninds.nih.gov/disorders/disorder_index.htm). The list of neurological disorders as at the date of filing is incorporated herein by reference.

In particular, the neurological disorder may be one commonly presenting in adulthood (such as multiple sclerosis, depression or bipolar disorder) or old age (such as mild cognitive impairment, Alzheimer's disease (AD) or another dementia, and Parkinson's disease (PD))

Further, the neurological disorder may be one commonly presenting in childhood such as attention deficit hyperactivity disorder (ADHD), autism or epilepsy.

The US National Institute of Health's National Institute of Mental Health (NIMH) lists the following as common neuropsychiatric disorders which it supports research into and which are herein included in the definition of "neurological disorder" in this disclosure:

Anxiety Disorders

Attention Deficit Hyperactivity Disorder (ADHD, ADD)

Autism Spectrum Disorders (ASD)

Bipolar Disorder (Manic-Depressive Illness)

Borderline Personality Disorder

Depression

Eating Disorders

Generalized Anxiety Disorder

Obsessive-Compulsive Disorder (OCD)

Panic Disorder

Prevention

Post-Traumatic Stress Disorder (PTSD)

Schizophrenia

Social Phobia (Social Anxiety Disorder)

Suicide Prevention

Further, the neurological disorder may be associated closely with a particular physical parameter which the sensor of the system is able to detect. Examples of parameters implicated with particular neurological disorders are set out in Table 1 below:

TABLE 1

| Physical Parameter | Neurological Disorder | Reference |
| --- | --- | --- |
| Pulse, blood pressure | Cerebrovascular disease, Alzheimer's | Nation 2013, http://www.ncbi.nlm.nih.gov/pubmed/24225352 |
| Skin Conductance | epilepsy | Poh 2012 DOI: 10.1212/WNL.0b013e318258f7f1 |
| Location | dementia | Yamakawa 2014 http://www.ncbi.nlm.nih.gov/pubmed/25369874 |
| Activity | ADHD | O'Mahoney 2014 http://www.ncbi.nlm.nih.gov/pubmed/24657100 |
| Voice | Parkinson's | Tanaka 2015 http://www.ncbi.nlm.nih.gov/pubmed/25712544 |
| Facial expressions | Autism | McIntosh 2006 www.ncbi.nlm.nih.gov/pubmed/16669800 |
| Use of phone | Depression | Thomee 2011 http://www.ncbi.nlm.nih.gov/pmc/ |

TABLE 1-continued

| Physical Parameter | Neurological Disorder | Reference |
|---|---|---|
| | | articles/PMC3042390/<br>Ikeda 2014<br>http://link.springer.com/article/<br>10.1007%2Fs12199-013-0373-3 |
| Use of social media | Depression | De Choudhury<br>http://research-srv.microsoft.com/pubs/<br>192721/icwsm_13.pdf |

As used herein, cognitive assessment test or cognitive test or cognitive function test includes any test which is able to provide meaningful information about an individual's cognitive function. This includes question and answer based tests, computerised "puzzle"-like tests as well as less formal tests, such as the individual's ability to respond to simple instructions such as to "wave your hand 5 times".

Specific examples of cognitive tests include:

validated cognitive assessments relevant to either the known neurological disorder of the patient or the suspected or possible neurological disorder indicated as a result of the analysis of the behavioural data by the computer system; or validated cognitive assessments to compare the cognitive function of the user with previous data for the user and/or validated and matched data for the general population or a particular disease group.

In particular embodiments, the cognitive assessment test is relevant to the older population and conditions such as dementia, AD or PD.

In further embodiments, the cognitive assessment test is relevant to children and conditions such as ADHD, autism or epilepsy.

In further embodiments, the cognitive assessment test relates to neuropsychiatric disorders including depression or eating disorders.

Examples of such validated cognitive assessment tests are set out in Table 2 below:

TABLE 2

| Disease | Test | Ref |
|---|---|---|
| ADHD | Stop signal test | Chamberlain SR (2011)<br>http://www.ncbi.nlm.nih.gov/<br>pubmed/21047621 |
| Alzheimer's | Paired associates learning | Blackwell AD (2004)<br>http://www.ncbi.nlm.nih.gov/<br>pubmed/14560064 |
| Parkinson's | Tower of London | Owen AM (1992)<br>http://www.ncbi.nlm.nih.gov/<br>pubmed/1486458 |
| Depression | Pattern recognition | Rock PL (2013)<br>http://www.ncbi.nlm.nih.gov/<br>pubmed/24168753 |
| Bipolar disorder | Sustained attention | Clark L (2005)<br>http://www.ncbi.nlm.nih.gov/<br>pubmed/15652878 |
| MS | Spatial working memory | Gmeindl L (2012)<br>http://www.ncbi.nlm.nih.gov/<br>pubmed/22059650 |

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

Figure 1:
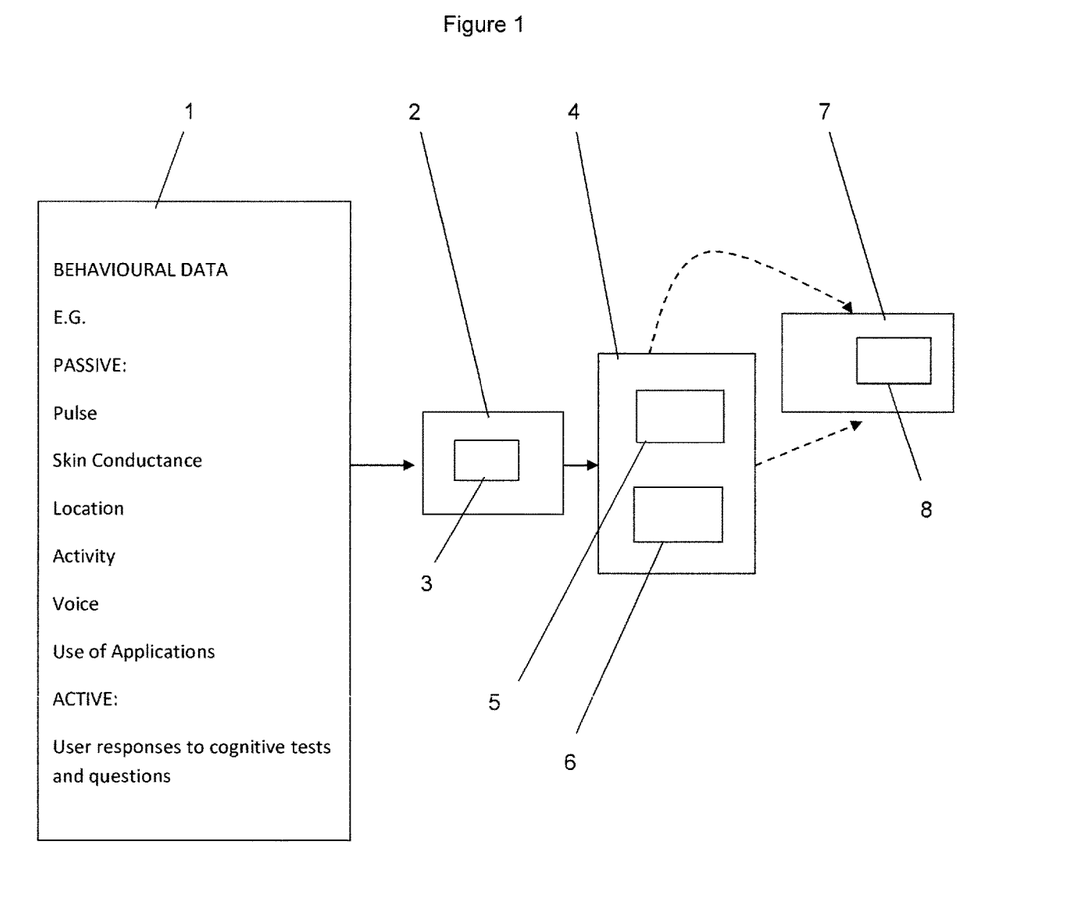
FIG. 1 shows, in schematic form, a system according to an embodiment of the present invention and the flow of data in a method according to a further embodiment of the present invention.

FIG. 1 shows, in schematic form, a system according to a general embodiment of the present invention. A user 1 exhibits a variety of behaviours which can be recorded as physical parameters of the user 1. These include behaviours which can be passively recorded, such as the user's pulse, skin conductance, body temperature, location, activity, voice or use of applications as well as behaviours which are actively monitored, such as the user's response to cognitive tests and questions. Further examples of behaviours/parameters are set out above.

One or more of these physical parameters of the user 1 are sensed by a wearable device 2 which includes at least one sensor 3 which is arranged to sense the physical parameter in question. The wearable device may be a specifically designed sensor, such as a wristband to measure pulse or skin conductance. The wearable device may be a watch, a band, glasses or a smartphone. Further examples of wearable devices are discussed above. The user may be presented with visual or audible information by the wearable device. Visual information may be displayed on a screen or projected onto a surface. Audible information may be delivered via a speaker or via headphones or an earpiece.

The data from the sensor 3 is passed to a local computing device 4 which has a processor 5, a memory 6 and optionally a display (not shown). The computing device 4 may be part of the wearable device or it may be a separate device such as a smartphone, tablet, laptop or desktop computer which is in communication with the wearable device 2. Such communication is preferably wireless, for example, 3 G, 4 G, Bluetooth or Wi-Fi, but may use a cable linking the devices.

The computing device 4 is optionally in communication with a remote server 7 which has a storage 8. The remote server may store baseline data for the user 1 or for general populations. The comparison of the behavioural data sensed by the sensor 3 may be carried out on the remote server 7. Alternatively, the computing device 4 may request baseline data for performing a comparison from the server. In certain embodiments, the computing device 4 stores data in its memory 5 which relates to the specific user, whilst the server 7 stores normative data relating to the population as a whole and/or specific data which is indicative of a particular condition or risk factor.

FIG. 1 also shows the flow of data in a method according to a general embodiment of the present invention. As shown by the arrows in FIG. 1, the behavioural data of the user 1 is detected by the wearable device 2 and fed to the processor 5 of a local computer 4 and may be stored in memory device 6. The data may be transmitted by the local computer 4 to a remote server 7 for storage or further analysis.

Figure 2:
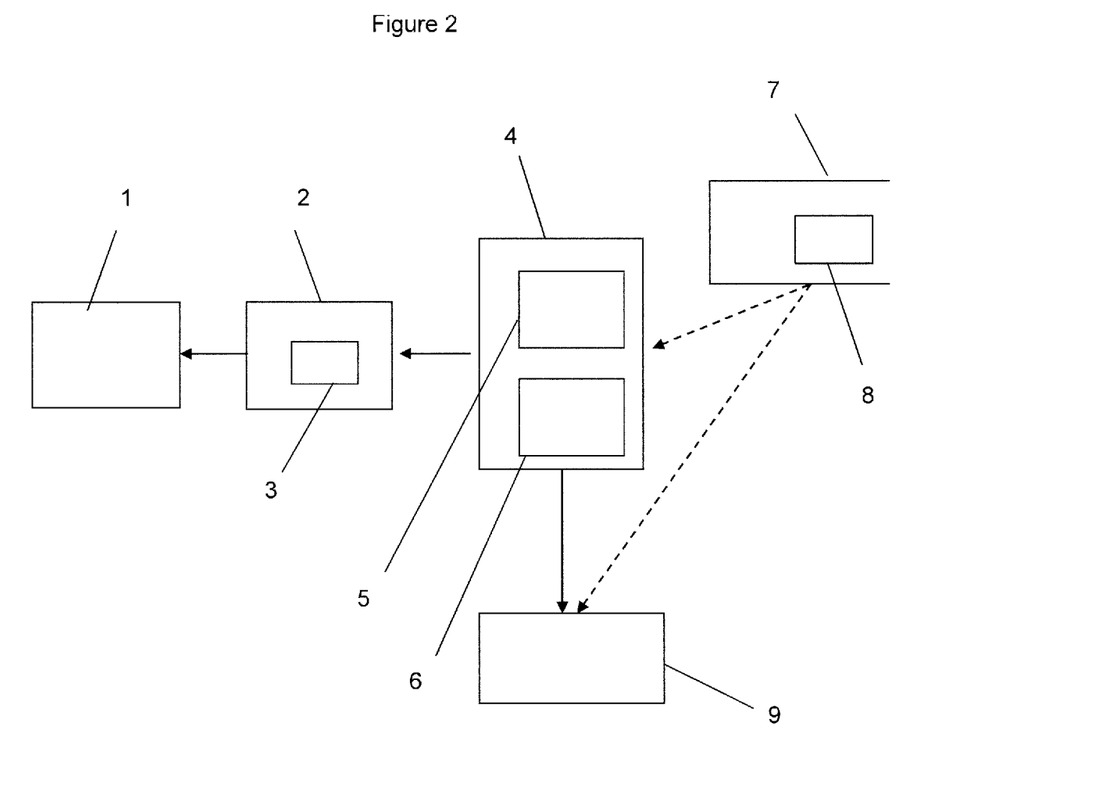
FIG. 2 shows the system of FIG. 1 with further data flows.

FIG. 2 shows the same outline system as in FIG. 1 with the addition of a doctor/carer 9 (or their computer interface). In the data flow shown in FIG. 2, the computing device 4 or, optionally, the remote server 7, following comparison of the data from the sensor 3 against the stored baseline data, initiates a cognitive test for the user to complete. This cognitive test may be initiated on the wearable device 2 if that device has a user interface (e.g. a smartphone, smartwatch) or on the user interface of the computing device 4. The user 1 may be prompted to complete the test by an audible, visual or sensory alert from the wearable device 2.

Following completion of the cognitive test, the results of the test are compiled and analysed by the processor 5 of the computing device 4, or by the remote server 7. Depending on the outcome of the test, the computing device 4 or, optionally, the remote server 7 can pass information regarding the user 1 to the doctor/carer 9, for example to alert the doctor/carer to a material change in the user's cognitive function following the user completing a cognitive test. The computing device 4 and/or the remote server 7 can also pass a further warning, notification and/or recommendation to the user 1 either through the wearable device 2 or the user interface of the computing device. Again, the user 1 may be alerted to this warning, notification or recommendation by an audible, visual or sensory alert.

Figure 3:
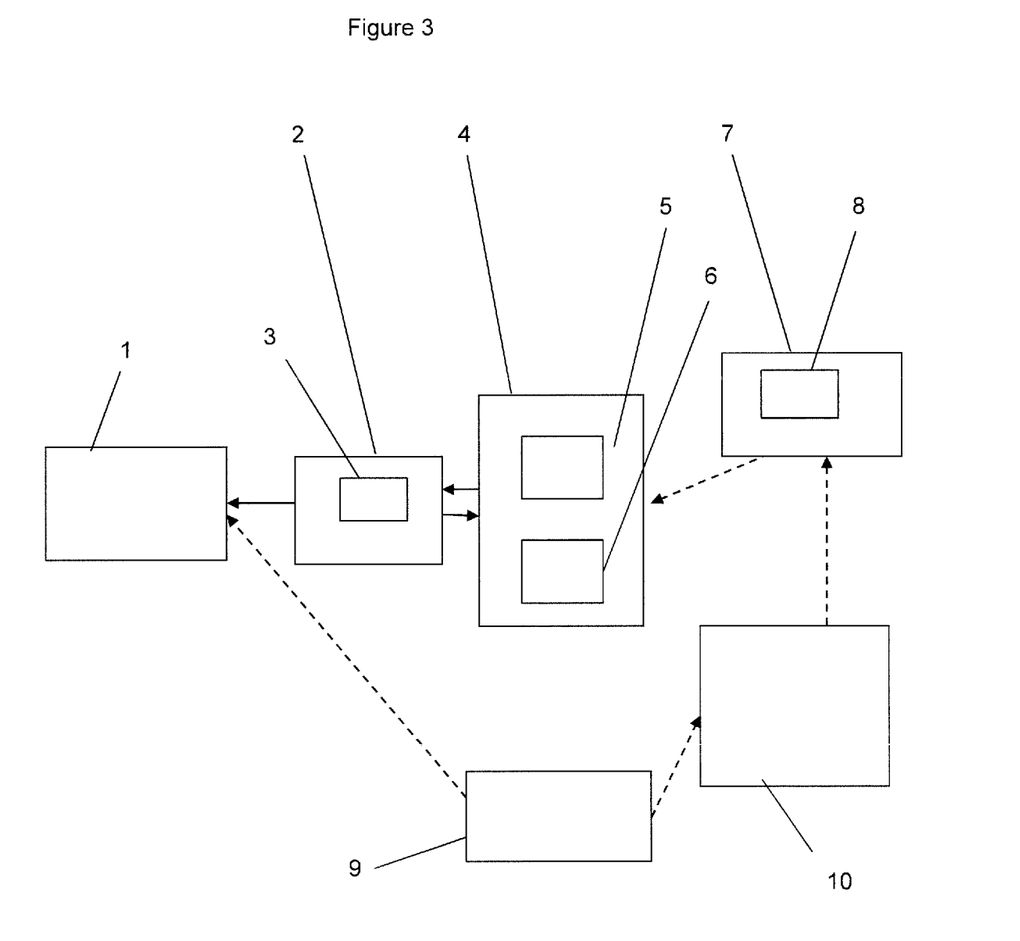
FIG. 3 shows possible further interactions in the system of FIG. 1.

FIG. 3 shows the same outline system as in FIGS. 1 and 2, but with the optional addition of a computer interface 10 for the doctor/carer 9 to connect and communicate with the remote server 7.

As shown in FIG. 3, the doctor/carer 9 can interact further with the user 1, either directly, or through either the local computer 4 and/or the wearable device 2, or through the remote server 7 (and thence through the local computer 4 and wearable device 2). This may be to initiate further tests, deliver specific messages to the user 1, or pass on instructions to the user 1 (for example that the user should take a particular medication, or refrain from certain activities).

EXAMPLES OF THE INVENTION

A number of example uses of the systems and methods according to embodiments of the present invention will now be described. These examples are intended to be representative of the range of possible uses that can be made and are not to be considered in any way limiting the uses that could be made of these systems and methods. The skilled person will also appreciate that the uses set out in the examples below can be readily modified, for example to monitor different attributes or inputs in order to be directed to a particular neurological condition.

The systems of embodiments of the invention are able to capture moment-to-moment information about cognition and other aspects of wellbeing in a way that has never before been practical, due to the always-on and highly sophisticated screens and graphics available in modern smartphones and the new wearable devices. Furthermore, being able to link this to contextual information about physical location, and physical activity through the smartphone-device interaction can allow cognitive tests to be triggered at relevant times as influenced by the behavioural data. For example, when in a pre-specified location or when sensed behaviour such as long periods of inactivity are detected. This allows real-world assessment of behaviour that until now has been objectively measurable only when sat at a computer or a in a clinic.

Example 1

Epilepsy

In one preferred embodiment of the invention, a system according to the invention is used to monitor a patient with a history of seizures. The patient may have been experiencing a worsening of symptoms or may have been prescribed new medication and the patient and doctor are therefore interested in ascertaining the impact on the course of the disease.

The wearable device is a band incorporating a sensor which is capable of monitoring skin conductance. Physical activity and location are measured via the wearable device itself which may include a GPS location device and/or accelerometers.

The sensor and the wearable device communicate with the patient's smartphone via a wireless connection, such as Bluetooth, and with a remote server via Wi-Fi or 4G signals (and over a physical backhaul network). The server stores and runs software relating to cognitive testing for epilepsy or other neurological disorders resulting in seizures. The server also stores, in a memory device, validated data sets for behavioural parameters of the general population and patients suffering from such neurological disorders. The server may also store specific data sets for behavioural parameters of the individual patient, as well as records of recent and historical data regarding the patient's behaviour, cognitive function and movement.

The patient has a nominated carer and a doctor who can be notified by the system and who can access the patient's data via a computer interface linked to the server through an internet connection.

The sensor repeatedly (and effectively continuously, for example by periodic sampling) and passively monitors the patient's skin conductance and transfers data to the wearable device for analysis. Software in either the smartphone, the wearable device or the server compares the user's data to reference baseline data for the individual and data sets for the general population and one or more relevant populations of patients and provides feedback to the patient and to the nominated carer and doctor in the form of messages indicating patient status.

The feedback to the patient may be in the form of simple statements or questions, such as "You are not 100% today, let's take a short test"; "Are you feeling ok?"; or "We have a message for you to call your doctor".

In the event that the behavioural data for the individual falls outside of normal values, the system will notify the user via the wearable device or smartphone to take a cognitive test or answer simple and appropriate questions regarding their current state of health.

The individual's response (or lack of response) to and performance in the cognitive test or questioning will be recorded by the system, assessed and the data compared to the reference data sets and a response generated substantially in real time. The response may indicate an absolute value of the physical parameter or a risk-measure indicating worsening of the neurological disorder or an impending seizure. The carer or doctor can be notified by the system that a risk factor is present and can act accordingly. The follow up action can be a phone call to the patient, instigating an emergency response to the known location of the individual, or triggering further cognitive assessments via the system. Data from the patient's location and state of physical activity can be used to further inform the risk assessment and the necessary or prompted action.

Example 2

Dementia

In another preferred embodiment of the invention, a system according to the invention is used to detect and record symptoms consistent with dementia in an elderly individual. The individual may live on their own and may not be aware of, or able to recall, symptoms when in later consultation with their doctor or carer.

The wearable device may be a watch or band connected via wireless technology to a smartphone. Alternatively, the wearable device may be embedded in an item of clothing or item of jewelry or may even be implanted on the body. The sensor includes at least a GPS device and optionally an accelerometer. The GPS device is used to determine when the individual leaves their normal premises. The accelerometer detects and measures periods of physical activity and inactivity.

The system passively monitors the sensor for unusual patterns of physical behaviour. The patterns of behaviour for an individual are typically set in advance by parameters in the system with input from the user and/or their carer or healthcare professional. One such example may be a rule regarding the user leaving the house outside set hours, for example, during the hours of 10 pm and 7 am. Alternatively or additionally the parameters may be learned by the computer system following a period acquiring background data for the particular individual.

Where the system detects unusual patterns of physical activity (i.e. patterns which are outside the parameters set in advance, whether in terms of location or specific activity or inactivity, or an unusual sequence of activity), it provides feedback to the individual. The feedback could be in the form of information, questions and/or cognitive tests sent to the smartphone. The response of the individual to this feedback assists in the elimination of false positives and provides further behavioural data that can be useful to the individual's medical team in understanding the individual's experience of dementia such as the duration/frequency of such events. Other interventions can also be triggered by the system for example by notification to the individual's carer (s), health professionals or emergency services such as automated phone call, text message or e-mail.

Feedback can also occur at pre-programmed times determined by the carer or doctor. For example a cognitive test can be activated every morning in order to provide the doctor with a more complete pattern of symptoms in between clinical assessments.

Example 3

Multiple Sclerosis

In a further preferred embodiment of the invention, the individual's coordination is monitored by the system based on the individual's behavioural data. The behavioural data in this embodiment comprises physical screen inputs, speed of response to stimuli during phone use, and voluntary and involuntary movements monitored via a sensor comprising an accelerometer.

Parameters summarising co-ordination are measured against the individual's personal history and/or disease-based norms.

If parameters deviate by more than a predetermined amount from the individual's personal norms or meet a predetermined set of criteria defining a likely relapse, symptom questions and cognitive tests are triggered by the system.

Responses from the co-ordination, symptom and cognitive parameters are summarised and compared with reference baseline and longitudinal data for the individual and data sets for the general population and relevant population of patients to infer risk of relapse or describe characteristics of change over time. If an increased risk of relapse is determined, a report summarising the parameters and inferences is sent to patient or clinician warning of a risk of relapse.

Example 4

Stress and Cognitive Function

In a further preferred embodiment of the invention, wearable sensors in the computer system detect blood pressure or heart rate along with physical activity in the individual. These values are monitored over time to determine an individual-specific pattern of normal blood pressure and heart rate during periods of inactivity. If blood pressure or heart rate exceeds parameters determined by these individual-specific values or predetermined general population cut-offs in the absence of physical activity, a cognitive test of attention is triggered by the computer system together with questions about current stress level.

If responses to the questions suggest high current stress levels, or cognitive test results show poor focus, possible remedial actions are suggested. These might include, for example, a relaxation exercise produced on the smartphone or wearable device. Data from the monitoring over time of blood pressure, heart rate, activity, cognitive test results and responses to questions about stress, are accrued over time and presented as feedback on the wearable or smartphone as graphic displays. This allows the individual to understand daily and long-term patterns of their stress and its effect on cognitive function.

Example 5

Mild Cognitive Impairment

In a further embodiment of the invention, the system is used to monitor an older adult considered to be at risk of dementia and who is showing some signs of mild cognitive impairment (MCI) such as poor or variable memory performance.

The system is utilised over a period of time which may be days, weeks or months to enable the individual and their doctor to better understand the extent and frequency of memory lapses. The individual's information may be compared with population data to determine current degree of impairment, predict prognosis or likely rate of worsening, and enable forward planning by the individual (e.g. employment and financial planning) and better understanding by their doctor of current range of memory problems and hence prevention and treatment options for the individual.

The system collects behavioural data relevant to known indicators of MCI, dementia, or dementia-related disease such as Alzheimer's and Parkinson's diseases. Such data may include use of the smartphone, physical activity, and voice parameters. The system initiates cognitive assessments during the period of monitoring. The cognitive assessments may be triggered in response to behavioural data sensed by the wearable device or at fixed time intervals.

The behavioural data is combined with cognitive performance scores and compared to population-based datasets. The observed and comparative data is interpreted to provide inferences regarding current risk of disease or change in recent health state. This information is passed to the health professional, individual, and/or carer.

Example 6

Effects of Sleep Deprivation/Fractionated Sleep

In a further embodiment of the invention, the system is used to monitor a person's sleep duration and/or quality.

The sensors in the wearable device measure the person's sleep duration and/or quality. In one embodiment, this is done by using an accelerometer to determine both the time at which the person enters and leaves sleep, as well as the proportion of the different types of sleep. Alternatively or additionally, the sensor(s) may monitor body temperature fluctuations and/or direct polysomnography to provide this information.

If the person's sleep deviates from the predetermined baseline for the individual by more than a certain amount, for example if the person obtains significantly less than the usual amount of sleep or if the person obtains less than a certain amount of deep sleep, a cognitive test can be initiated after the person has awoken.

The recorded parameters of the sleep and the results of the cognitive test(s) and, optionally, the person's recent sleep and cognition history (last few days—as recorded by the system) are compared with a database and used to determine a risk index for that person. Several methodologies for the assessment of sleep disorders are known in the art and an appropriate methodology may be selected based on the medical history of the individual. For example, the apnea-hypopnea index has utility in relation to risk of traffic accidents and the SCOPA Sleep scale is useful in individuals with Parkinson's Disease and other populations.

Depending on the outcome of the comparison, and in particular if the risk index exceeds certain thresholds, warnings are displayed to the user on the display.

The system could find particular use in relation to individuals who are employed in particular high-risk occupations, such as air traffic control, pilots, heavy machinery operators, surgeons, in which cases, warnings could also be sent to an employer or supervisor.

Sleep patterns are also a risk indicator for patients with certain neurological disorders, including Parkinson's Disease, and the system could also find use in monitoring the patient for evidence of progression of disease and/or response to medical treatment.

Example 7

Assessment of Agents for the Treatment of Neurological Disorders

In further embodiments of the present invention, the system is used in the clinical development of agents for the treatment of neurological disorders.

The system can assist in improving clinical trials by providing a more accurate baseline from which to measure a treatment's effects and a new means to remotely monitor the safety or efficacy of new drugs being tested. These technological developments are urgently needed because approval rates for new brain-related drugs are low, causing pharmaceutical companies to seek better ways to run clinical trials and more accurate ways to target individuals who may be at a high risk of disorders such as Alzheimer's disease.

Real time mobile cognitive monitoring has the potential to revolutionise the way clinical trial monitoring of cognition for both safety and efficacy can occur. Safety and efficacy endpoints are problematic to assess using current computerized cognitive assessments.

The system presents cognitive tests and other questions on a wearable (e.g. watch) or smartphone device. It therefore collects information about cognitive performance in the patient's own environment rather than in laboratory or clinical contexts. Cognitive tests and other questions are triggered at fixed timepoints or in response to sensed behaviour (e.g. periods of inactivity of a given duration). These data provide an accurate 'baseline' of cognitive performance and show individual-level variation across the day or longer periods.

This individual-level baseline data can then be compared with data collected using the same system when a patient is taking part in the active or placebo arm of a clinical trial. The pattern of data collected in the two conditions is compared to provide a more accurate assessment of the effect of the drug or other intervention and any variability of this effect that can be attributed to time-related factors such as hours of waking and sleep, timing of administration of drugs/interventions, daily patterns of physical activity.

This more frequent data collection increases the power of clinical trials by increasing the probability of detecting true effects of an intervention among the environmental 'noise' and without the drawbacks of clinical and lab settings (e.g. white coat syndrome). This improved signal-to-noise ratio can allow companies to detect significant drug effects in smaller samples, thereby accelerating the drug development process.

A second use for systems according to embodiments of the invention in clinical trials is to allow long-term infrequent cognitive monitoring of the effects of an intervention. This makes longer, more representative and less localised clinical trials logistically practical by substituting remote monitoring for more expensive face-to-face interactions. This is particularly important in allowing companies to monitor large numbers of patients for potential cognitive safety concerns over long periods of time, potentially allowing regulators to make new treatments available sooner where there is high unmet medical need.

A third use for systems according to embodiments of the invention is in the cognitive monitoring of the effects of an agent following the grant of a marketing authorisation or other form of product license by the competent regulatory authority such as the Food and Drug Administration (FDA) in the US or the European Medicines Agency (EMA) in the European Union. Holders of a marketing authorisation are under a regulatory duty to conduct an ongoing pharmacovigilance assessment for each agent and may be required to conduct post-marketing clinical studies (also known as Phase IV studies) to assess, for example, the long-term side effects of the agent. The methods and systems of the invention are thus applicable to the continued assessment of the risk:benefit of agents not only during clinical development but also following the grant of marketing authorisation.

Example 8

Assessment of Whether a Treatment is of Benefit to a Patient

In further embodiments of the present invention, the system is used to assess whether a particular treatment for a neurological disorder is safe, effective or of benefit to a patient. The system may also be used to assess whether a treatment for a disorder is having any effect whether intended or unintended on the patient's cognitive function. The system may also be used to investigate the consequences for the patient if the dose or dosing schedule of a particular treatment is changed.

The system presents cognitive tests and other questions on a wearable (e.g. watch) or smartphone device. It therefore collects information about cognitive performance in the patient's own environment rather than in laboratory or clinical contexts. Cognitive tests and other questions are triggered at fixed timepoints or in response to sensed behaviour (e.g. periods of inactivity of a given duration). These data provide an accurate 'baseline' of cognitive performance and show individual-level variation across the day or longer periods.

The baseline performance may be built up prior to prescription of a course of treatment for a patient.

This individual-level baseline data can then be compared with data collected using the same system when the patient is undergoing the prescribed course of treatment. The pattern of data collected before and after the commencement of the course of treatment is compared to provide a more accurate assessment of the effect of the treatment and any variability of this effect that can be attributed to time-related factors such as hours of waking and sleep, timing of administration of drugs/interventions, daily patterns of physical activity.

The data collected for an individual patient can be used by a healthcare professional to assess the safety, efficacy or benefit of a treatment an individual patient and the effects of changes to the dosing regimen for the treatment.

The systems and methods of the above embodiments may be implemented in a computer system (in particular in computer hardware or in computer software) in addition to the structural components and user interactions described.

The term "computer system" includes the hardware, software and data storage devices for embodying a system or carrying out a method according to the above described embodiments. For example, a computer system may comprise a central processing unit (CPU), input means, output means and data storage. Preferably the computer system has a monitor to provide a visual output display (for example in the design of the business process). The data storage may comprise RAM, disk drives or other computer readable media. The computer system may include a plurality of computing devices connected by a network and able to communicate with each other over that network.

The methods of the above embodiments may be provided as computer programs or as computer program products or computer readable media carrying a computer program which is arranged, when run on a computer, to perform the method(s) described above.

The term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting.

Various changes to the described embodiments may be made without departing from the spirit and scope of the invention.

REFERENCES

Pulse pressure is associated with Alzheimer biomarkers in cognitively normal older adults. Nation D A et al Neurology. 2013 Dec. 3; 81 (23):2024-7, Autonomic changes with seizures correlate with postictal EEG suppression, Poh M Z et al Published online before print Apr. 25, 2012, doi: http://dx.doi.org/10.1212/WNL.0b013e318258f7f1 Neurology WNL.0b013e318258f7f1

Yamakawa M et al, Caring for early-onset dementia with excessive wandering of over 30 kilometres per day: a case report (Psychogeriatrics. 2014 December; 14 (4):255-60. doi: 10.1111/psyg.12075. Epub 2014 Nov. 4)

O'Mahony N et al, Objective diagnosis of ADHD using IMUs (Med Eng Phys. 2014 July; 36(7):922-6. doi: 10.1016/j.medengphy.2014.02.023. Epub 2014 Mar. 20)

Tanaka Y et al, Voice features of Parkinson's disease patients with subthalamic nucleus deep brain stimulation (J Neurol. 2015 Feb. 26. [Epub ahead of print])

McIntosh D N et al, When the social mirror breaks: deficits in automatic, but not voluntary, mimicry of emotional facial expressions in autism (Dev Sci. 2006 May; 9(3): 295-302)

Thomee S et al, Mobile phone use and stress, sleep disturbances, and symptoms of depression among young adults—a prospective cohort study (MC Public Health. 2011; 11: 66. Published online 2011 Jan. 31. doi: 10.1186/1471-2458-11-66)

Association between mobile phone use and depressed mood in Japanese adolescents: a cross-sectional study (Environmental Health and Preventive Medicine Volume 19, Issue 3, pp 187-193)

De Choudhury M et al, Predicting Depression via Social Media,

Chamberlain S R et al, Translational approaches to fronto-striatal dysfunction in attention-deficit/hyperactivity disorder using a computerized neuropsychological battery (Biol Psychiatry 2011 Jun. 15; 69(12):1192-203. doi: 10.1016/j.biopsych. 2010.08.019. Epub 2010 Nov. 3.)

Blackwell A D et al, Detecting dementia: novel neuropsychological markers of preclinical Alzheimer's disease (Dement Geriatr Cogn Disord. 2004; 17(1-2):42-8. Epub 2003 Oct. 13).

Owen A M et al, Fronto-striatal cognitive deficits at different stages of Parkinson's disease (Brain. 1992 December; 115 (Pt 6):1727-51).

Rock P L et al, Cognitive impairment in depression: a systematic review and meta-analysis (Psychol Med. 2013 Oct. 29:1-12. [Epub ahead of print])

Clark L et al, Sustained attention-deficit confirmed in euthymic bipolar disorder but not in first-degree relatives of bipolar patients or euthymic unipolar depression (Biol Psychiatry. 2005 Jan. 15; 57 (2):183-7).

Gmeindl L et al, Deconstructing spatial working memory and attention deficits in multiple sclerosis (Neuropsychology. 2012 January; 26(1):57-70. doi: 10.1037/a0026213. Epub 2011 Nov. 7).

Marinus J et al, Assessment of sleep and sleepiness in Parkinson's disease (SLEEP, Vol. 26, No. 8, 2003)

Teran-Santos J et al, The association between sleep apnea and the risk of traffic accidents (N Engl J Med 1999; 340:847-51.)

All references referred to above are hereby incorporated by reference.

The invention claimed is:

1. A method for analysis of cognitive function and treatment, the method comprising:
   sending, by a server, a request to a wearable device for sensor data, wherein the sensor data relates to at least one physical parameter of a user;
   receiving, at the server from the wearable device, sensor data;
   sending, by the server, instructions to the wearable device to present a scientifically-validated cognitive test to obtain data about the user's cognitive function, based on the sensor data;
   receiving, at the server from the wearable device, results of the scientifically-validated cognitive test;
   comparing, by the server, the results against a predetermined baseline, said baseline including one or more of: historic data of the user; relevant scientifically-validated data sets for general populations; and relevant scientifically-validated data sets for populations with specific neurological disorders;
   determining, at the server, based on the comparison and the received sensor data, an assessment of the user's cognitive function;
   sending, by the server, a notification to the wearable device based on the assessment;
   sending, by the server, instructions to the wearable device to present a second test based on the results of the scientifically-validated cognitive test; and
   receiving, by the server, the results of the second test and including them in the assessment of the user.

2. The method of claim 1, wherein the at least one physical parameter includes brain-wave activity, heart rate, body temperature, blood pressure, voice pitch, talking speed, reaction times, use of smartphone, an amount of physical motion, facial expression, skin conductance, or location data.

3. The method of claim 1, wherein the predetermined baseline includes specific population data for a neurological disorder, wherein the disorder is selected from a group of disorders comprising: Alzheimer's, Parkinson's, dementia, attention deficit hyperactivity disorder (ADHD), depression, bipolar disorder or mild cognitive impairment (MCI).

4. The method of claim 3, wherein the scientifically-validated cognitive test includes at least one of the following: stop signal test; paired associates learning; Tower of London, pattern recognition; sustained attention; or spatial working memory.

5. The method of claim 4, further comprising evaluating, by the server, an effectiveness of a treatment after a change in a treatment dosage based on the assessment and known treatment data.

6. The method of claim 4, further comprising sending an indication of the safety or effectiveness to a healthcare entity conducting a clinical study of a treatment for depression, Alzheimer's, Parkinson's, dementia, attention deficit hyperactivity disorder (ADHD), bipolar disorder or mild cognitive impairment (MCI).

7. The method of claim 6, wherein the step of sending an indication of the safety or effectiveness to a healthcare entity comprises sending an indication of the safety or effectiveness to a healthcare entity conducting a clinical study of a treatment for depression.

8. The method of claim 1, wherein the method assesses a user suffering from stress,
   wherein the at least one physical parameter comprises blood pressure, heart rate, or physical activity, and
   wherein the scientifically-validated cognitive test is configured to assess an attention of the user.

9. The method of claim 1, wherein the method monitors a user considered to be at risk of dementia,
   wherein the at least one physical parameter comprises use of smartphone, physical activity, or voice parameters, and
   wherein the scientifically-validated cognitive test is configured to assess a memory of the user.

10. The method of claim 1, wherein the method is used in clinical development of agents for neurological disorder treatments, and
    wherein baseline data for the user is collected and compared, by the server, with data collected when the user is taking part in an active or placebo arm of a clinical trial.

11. The method of claim 1, wherein the method assesses whether a treatment benefits the user, and
    wherein baseline data for the user is collected and compared, by the server, with data collected when the user is undergoing a prescribed course of treatment.

12. A wearable device for assessment of cognitive function and treatment, comprising:
    one or more processors; and
    a plurality of sensors operatively coupled to the one or more processors configured to measure at least one physical parameter of a user;
    the one or more processors further configured to compare the measurements to predetermined threshold values and determine to present a scientifically-validated cognitive test to the user to obtain data about the user's cognitive function, based on the comparison of the measurements;
    a user interface controlled by the one or more processors configured to present the scientifically-validated cognitive test to the user;
    a memory operatively coupled to the one or more processors configured to record results of the scientifically-validated cognitive test, wherein the one or more processors is further configured to compare the results of the scientifically-validated cognitive test to a predetermined baseline stored in the memory, said baseline including one or more of: historic data of the user; relevant scientifically-validated data sets for general populations; and relevant scientifically-validated data sets for populations with specific neurological disorders, and determine, based on the comparison and the at least one measured physical parameter, an assessment of the user's cognitive function; and
    the user interface and the one or more processors further configured to display a notification regarding the assessment;
    wherein the user interface and one or more processors are further configured to present a second test based on the results of the scientifically-validated cognitive test, wherein the memory and the one or more processors are further configured to record results of the second test and include results of the second test in the determination of the assessment of the user.

13. The wearable device of claim 12, wherein the at least one physical parameter includes brain-wave activity, heart rate, body temperature, blood pressure, voice pitch, talking speed, an amount of physical motion, facial expression, skin conductance, or location.

14. The wearable device of claim 13, wherein the predetermined baseline includes specific population data for a neurological disorder, wherein the disorder is selected from a group of disorders comprising: Alzheimer's, Parkinson's, dementia, attention deficit hyperactivity disorder (ADHD), depression, bipolar disorder or mild cognitive impairment (MCI).

15. The wearable device of claim 14, wherein the scientifically-validated cognitive test includes at least one of the following tests:
   stop signal test; paired associates learning; Tower of London, pattern recognition;
   sustained attention; or spatial working memory.

16. The wearable device of claim 15, wherein the plurality of sensors includes a GPS, accelerometer, camera, or a heart rate monitor.

17. The wearable device of claim 15, wherein the one or more processors are further configured to evaluate an effectiveness of a treatment after a change in a treatment dosage based on the assessment and known treatment data.

18. The wearable device of claim 17, further comprising a transceiver operatively coupled to the one or more processors configured to send an indication of the effectiveness and the assessment to a healthcare entity conducting a clinical study for depression.

19. A computer readable medium operatively connected to one or more processors that configures a wearable device for assessment of the cognitive function and treatment, comprising a plurality of instructions that when executed by the one or more processors cause the wearable device to:
   measure at least one physical parameter of a user periodically using a plurality of sensors connected to the wearable device;
   compare the measurements to predetermined threshold values;
   determine to present a scientifically-validated cognitive test to the user through a user interface of the wearable device to obtain data about the user's cognitive function, based on the comparison of the measurements;
   present the scientifically-validated cognitive test through the user interface;
   record results of the scientifically-validated cognitive test to a memory of the wearable device, including response times or reaction times of the user;
   compare the results of the scientifically-validated cognitive test to a predetermined baseline, said baseline including one or more of: historic data of the user; relevant scientifically-validated data sets for general populations; and relevant scientifically-validated data sets for populations with specific neurological disorders;
   determine, based on the comparison and the at least one measured physical parameter, an assessment of the user's cognitive function the user;
   display an alert through the wearable of the assessment based on the determination;
   to present a second test through the user interface based on the results of the scientifically-validated cognitive test, the memory and the one or more processors to record results of the second test and include results of the second test in the determination of the assessment of the user.

20. The computer readable medium of claim 19, wherein the at least one plurality of physical parameter includes brain-wave activity, heart rate, body temperature, blood pressure, voice pitch, talking speed, an amount of physical motion, or location.

* * * * *